United States Patent [19]

Kranz et al.

[11] Patent Number: 5,583,275
[45] Date of Patent: Dec. 10, 1996

[54] ALKYLATION OF OLEFINS UTILIZING MIXTURES OF ISOPARAFFINS

[75] Inventors: Ken E. Kranz; James K. Millard, both of Kansas City, Mo.

[73] Assignee: Stratco, Inc., Leawood, Kans.

[21] Appl. No.: 293,049

[22] Filed: Aug. 19, 1994

[51] Int. Cl.$^6$ ............................................. C07C 2/58
[52] U.S. Cl. ..................... 585/709; 585/331; 585/721
[58] Field of Search ......................... 585/709, 331, 585/721

[56] References Cited

U.S. PATENT DOCUMENTS

| | | | |
|---|---|---|---|
| 2,347,317 | 4/1944 | Gibson | 260/683.4 |
| 2,405,993 | 8/1946 | Burk | 196/78 |
| 2,509,028 | 5/1950 | Abrams et al. | 260/683.4 |
| 3,045,055 | 7/1962 | Van Pool et al. | 260/683.48 |
| 3,211,803 | 10/1965 | Chapman | 260/683.49 |
| 3,502,569 | 3/1970 | Hervert | 208/49 |
| 4,225,740 | 9/1980 | Chapman et al. | 585/719 |
| 4,262,155 | 4/1981 | Hutson, Jr. | 585/331 |
| 4,276,439 | 6/1981 | Hutson et al. | 585/720 |
| 4,513,165 | 4/1985 | Van Pool | 585/723 |
| 5,382,744 | 1/1995 | Abbott et al. | 585/709 |

OTHER PUBLICATIONS

J. Van Steenis and H. I. Watgerman. Alkylation of Isopentane with Isopentane in the Presence of Concentrated Sulphuric Acid. Recueil des Travaux. Chimiques des Pays–Bas. vol. 67. 1948.

B. T. Brooks, et al. Eds. Chemistry of Petroleum Hydrocarbons. vol. 3. Reinhold, N.Y. 1955, pp. 393–394.

Abstract of a Russian paper. D. V. Mushenko. Alkylation of Butylenes with Isopentane. Trudy Vsesoyuz Nauch–Issledovatel. Inst. Neftekhim. Protessov, 1960. No. 3, pp. 210–213.

Primary Examiner—Asok Pal
Assistant Examiner—Bekir L. Yildirim
Attorney, Agent, or Firm—J. Mark Gilbreth

[57] ABSTRACT

Disclosed is an alkylation process in which $C_3$ to $C_5$ olefins are reacted with an isoparaffin mixture of isobutane and isopentane in the presence of a catalyst. Varying the amount of isopentane present in the mixture can control and/or eliminate the amount of isopentane produced in the alkylation reaction. The disclosed reaction has an improved alkylation yield, and also produces an alkylate having a lowered Reid Vapor Pressure and results in lowered olefin content for reformulated gasoline.

15 Claims, 13 Drawing Sheets

Bench-scale Alkylation Pilot Plant

ALKYLATION OF OLEFINS UTILIZING MIXTURES OF ISOPARAFFINS

BACKGROUND OF THE INVENTION

1. Field of the Invention

The present invention relates to alkylation. In another aspect, the present invention relates to the alkylation of olefins utilizing isoparaffins. In still another aspect, the present invention relates to the alkylation of $C_3$ to $C_5$ olefins utilizing a mixture of $C_4$ and $C_5$ isoparaffins. In yet another aspect, the present invention relates to the alkylation of $C_3$ to $C_5$ olefins utilizing a suitable mixture of $C_4$ and $C_5$ isoparaffins to increase alkylation yield. In still yet another aspect, the present invention relates to the alkylation of $C_3$ to $C_5$ olefins utilizing a suitable mixture of $C_4$ and $C_5$ isoparaffins to produce a resulting alkylation product having an improved Reid Vapor Pressure ("RVP").

2. Description of the Related Art

Alkylation is a well known refinery process for converting light gaseous olefins into high-octane gasoline components.

As practiced commercially, alkylation generally involves reacting isobutane with $C_3$ to $C_5$ olefins in the presence of an acid catalyst, typically either hydrofluoric acid or sulfuric acid. The resulting alkylate product comprises predominately $C_7$ to $C_9$ isoparaffins, along with lesser amounts of lighter and heavier isoparaffins in the $C_6$ to $C_{12}$ range, and some isopentane.

Recent reformulated gasoline specifications require a reduction in both the Reid Vapor Pressure ("RVP") and the olefin content. Alkylate is a low vapor pressure, high octane gasoline blending component containing no olefins. Thus, it helps refiners meet the new reduced RVP and reduced olefin content specifications. Additionally, alkylate burns cleanly, resulting in lower levels of undesired emisisons from gasoline engines.

U.S. Pat. No. 2,347,317, issued Apr. 25, 1944 to Gibson, discloses a process for converting relatively low-boiling hydrocarbons to motor fuel hydrocarbons in the presence of hydrofluoric acid. As disclosed, the process of U.S. Pat. No. 2,347,317 generally involves reacting a mixture of isobutane, normal butane, and hydrofluoric acid in excess of that required to form an azeotropic mixture with the isobutane. Distillation of the resulting product produces an overhead distillate mixture of hydrofluoric acid and isobutane, which is then cooled and separated into a hydrofluoric liquid phase and an isobutane liquid phase. The process of U.S. Pat. No. 2,347,317 is also disclosed as being especially advantageous in a combination isomerization-alkylation process in which normal butane is isomerized to isobutane in the presence of hydrofluoric acid. Gibson does disclose that in isomerizing normal pentane, isobutane is generally also produced, and that the combined isobutane and isopentane may be subjected to alkylation. However, Gibson does not disclose or teach that the production of isopentane can be controlled by varying the ratio of isobutane to isopentane, that the yield of the alkylation can be controlled by varying the ratio of isobutane to isopentane, or that the RVP of the alkylated product can be controlled by varying the ratio of isobutane to isopentane.

U.S. Pat. No. 2,405,993, issued Aug. 20, 1946 to Burk discloses the alkylation of higher molecular weight hydrocarbons with isopentane, and that alkylation with isopentane results in the production of isobutane. Burk further discloses that isopentane or mixtures of isopentane and isobutane may be reacted with hydrocarbons of more than five carbon atoms such that products in the gasoline range are obtained. However, Burk does not disclose or teach that production of isopentane can be controlled by varying the ratio of isobutane to isopentane, that the yield of the alkylation can be controlled by varying the ratio of isobutane to isopentane, or that the RVP of the alkylated product can be controlled by varying the ratio of isobutane to isopentane.

U.S. Pat. No. 2,509,028, issued May 23, 1950 to Abrams et al. discloses a method of producing gasoline by alkylation in which an entire alkylation reaction mixture containing hydrofluoric acid catalyst is introduced into a fractionating unit. In the unit the isoparaffins are reformed by further contact with the hydrogen fluoride catalyst under conditions which maintain material of the gasoline-boiling range and higher in liquid form, while lighter material, including hydrogen fluoride, vaporizes. Abrams et al. do not disclose or teach that production of isopentane can be controlled by varying the ratio of isobutane to isopentane, that the yield of the alkylation can be controlled by varying the ratio of isobutane to isopentane, or that the RVP of the alkylated product can be controlled by varying the ratio of isobutane to isopentane.

U.S. Pat. No. 3,045,055, issued Jul. 17, 1960 to Van Pool et al. generally discloses a process for the alkylation of a isoparaffin and the reforming of a hydrocarbon wherein each operation is arranged to benefit the other. Specifically, the process as disclosed by Van Pool et al. generally includes alkylation of an isoparaffin and an olefin in the presence of a hydrogen fluoride catalyst to obtain an alkylate effluent comprising an alkylate product, organic fluorides and normal paraffin. Van Pool et al. disclose that the charge materials introduced into the alkylation zone may include propylene, butylenes, amylenes, isobutane, isopentane, propyl fluorides, butyl fluorides, and amyl fluorides. Van Pool et al. further disclose that the preferred alkylation charge is an olefin-isoparaffin, preferably butylenes-isobutane. Van Pool et al. do not disclose or teach that production of isopentane can be controlled by varying the ratio of isobutane to isopentane, that the yield of the alkylation can be controlled by varying the ratio of isobutane to isopentane, or that the RVP of the alkylated product can be controlled by varying the ratio of isobutane to isopentane.

U.S. Pat. No. 3,211,803, issued Oct. 12, 1965 to Chapman discloses an alkylation process for the elimination of heavy alkylate utilizing both alkylation and reforming. Chapman does not disclose or teach that production of isopentane can be controlled by varying the ratio of isobutane to isopentane, that the yield of the alkylation can be controlled by varying the ratio of isobutane to isopentane, or that the RVP of the alkylated product can be controlled by varying the ratio of isobutane to isopentane.

U.S. Pat. No. 3,502,569, issued Mar. 24, 1970 to Hervert discloses a process for the production of high octane motor fuel by alkylation and reforming. Hervert discloses that alkylation may be carried out by the catalytic alkylation of isobutane and/or isopentane with propylenes, butylenes and amylenes. Specifically Hervert discloses alkylating isobutane with $C_4$ mono-olefin in the presence of an acid catalyst to produce an alkylate product containing dimethylhexanes. This alkylate is then separated into various fractions based on octane content. The lower-octane fraction is then reformed by admixture with hydrogen and a reforming catalyst. Finally, a portion of the reformate is commingled with the high-octane alkylate fraction to produce a suitable motor fuel alkylate. Hervert does not disclose or teach that production of isopentane can be controlled by varying the ratio of isobutane to isopentane, that the yield of the alkylation can be controlled by varying the ratio of isobutane to isopentane, or that the RVP of the alkylated product can be controlled by varying the ratio of isobutane to isopentane.

Recent patents also generally disclose the use of mixtures of isoparaffins. See U.S. Pat. No. 4,225,740, at col. 3, lines 11–16; U.S. Pat. No. 4,276,439, at col. 2, lines 14–18; and U.S. Pat. No. 4,513,165 at col. 2, lines 39–41. Like the above cited patents, these recent patents also do not disclose or teach that production of isopentane can be controlled by varying the ratio of isobutane to isopentane, that the yield of the alkylation can be controlled by varying the ratio of isobutane to isopentane, or that the RVP of the alkylated product can be controlled by varying the ratio of isobutane to isopentane.

As recent reformulated gasoline specifications require a reduction in the Reid Vapor Pressure ("RVP") and a reduction in the olefin content, there is a need in the art for an alkylation process that will produce alkylate that has a lowered RVP and that will help lower the olefin content of the gasoline pool.

As production of $C_5$ paraffins increases its presence in the final gasoline pool and thus negatively effects the desired or target RVP and resultant yield, there is a need in the art for an alkylation process that will reduce, eliminate or control the production of $C_5$ paraffins in the alkylation process.

Other needs of the art will become evident to those of skill in the alkylation art upon reading this specification.

SUMMARY OF THE INVENTION

It is an object of the present invention to provide an alkylation process that will produce alkylate having an improved RVP.

It is another object of the present invention to provide an alkylation process that will reduce, eliminate or control the production of $C_5$ paraffins in the alkylation process.

It is yet another object of the present invention to provide an alkylation process in which that alkylation yield can be increased.

These and other objects of the present invention will become evident to those of skill in the alkylation art upon review of this specification.

According to one embodiment of the present invention there is provided a process for alkylating $C_3$ to $C_5$ olefins with an isoparaffin mixture comprising isobutane and isopentane in which the amount of isopentane produced in the reaction is less than or equal to the amount of isopentane consumed in the reaction. The process generally includes contacting the olefins with an isoparaffin mixture comprising isobutane and isopentane in the presence of an alkylation catalyst under conditions suitable to cause alkylation. For the alkylation of $C_3$ and $C_4$ olefins, the isoparaffin mixture comprises in the range of about 1 to about 10 weight percent isopentane based on the total weight of isobutane and isopentane. For the alkylation of $C_5$ olefins, the isoparaffin mixture comprises in the range of about 15 to about 35 weight percent isopentane based on the total weight of isobutane and isopentane.

According to another embodiment of the present invention there is provided a process for producing alkylate having an alkylate motor octane number greater than the alkylate research octane number. The method generally includes contacting $C_3$ to $C_5$ olefins with an isoparaffin mixture comprising isobutane and isopentane in the presence of an alkylation catalyst under conditions suitable to cause alkylation. In this embodiment, the isoparaffin mixture comprises greater than about 40 weight percent isopentane based on the total weight of isobutane and isopentane.

According to yet another embodiment of the present invention there is provided a method of improving the known alkylation processes in which $C_3$ to $C_5$ olefins are reacted with isobutane in the presence of an alkylation catalyst and isopentane is produced as an alkylation product. The net production of isopentane in the alkylation process is generally undesirable. The improvement of this embodiment generally includes the use of an isoparaffin mixture of isobutane and isopentane for the alkylation of $C_3$ to $C_5$ olefins. In this embodiment, the amount of isopentane present in the isoparaffin mixture is in an amount sufficient to eliminate the net production of isopentane.

DETAILED DESCRIPTION OF THE INVENTION

Figure 1:
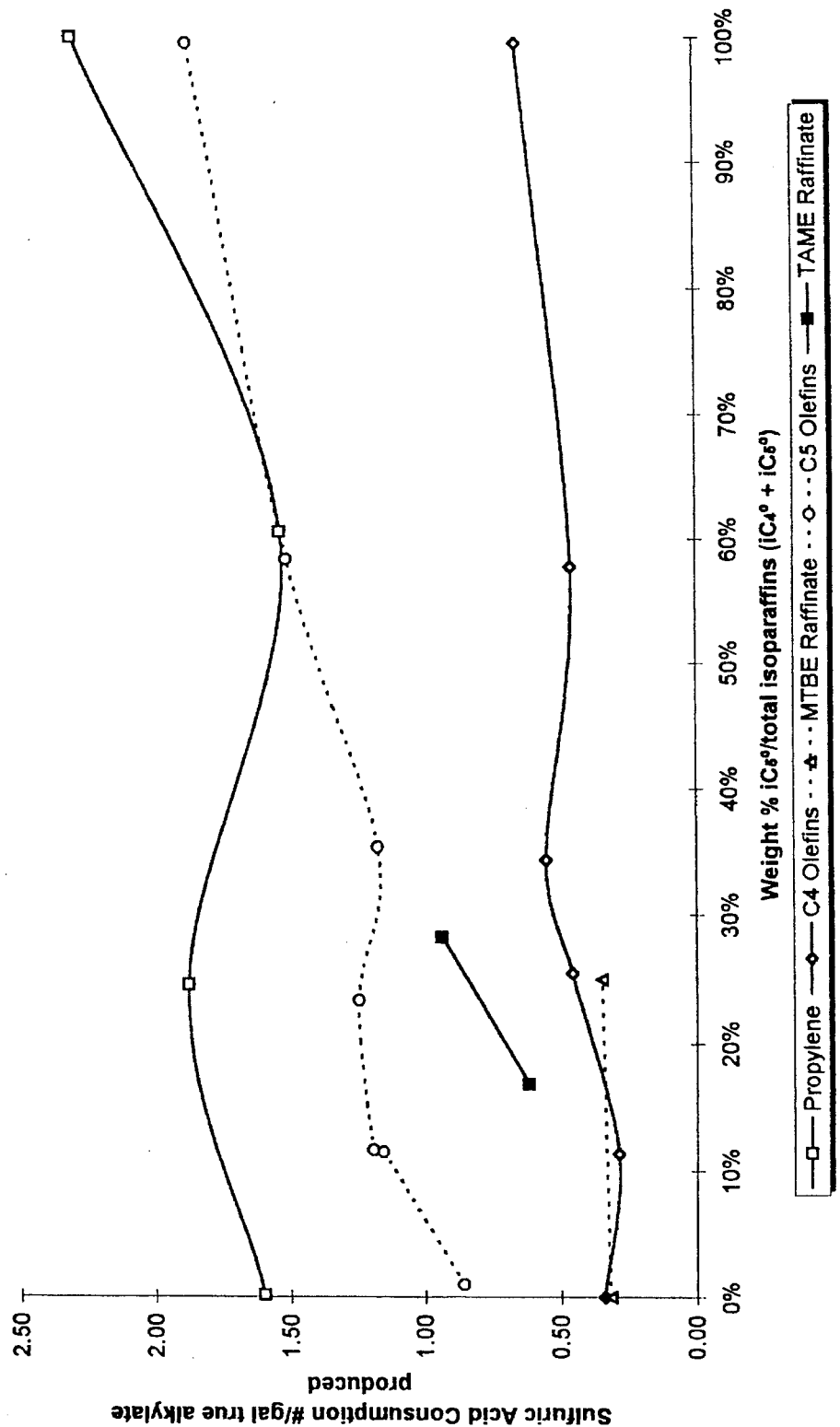
FIG. 1 is a graph that shows the relationship between sulfuric acid catalyst consumption and the weight percent of isopentane in the isobutane and isopentane feed for various olefins.

The inventors have discovered that alkylation processes may be improved by varying the ratios of isoparaffins in the alkylation feed. Among other things, the inventors have specifically discovered that in alkylation processes, the net production of isopentane during the alkylation reaction may be controlled, reduced and even eliminated by varying the ratios of the isoparaffin components in the alkylation feed, that the alkylation yield may be controlled by varying the ratios of the isoparaffin components in the alkylation feed, and that the Reid Vapor Pressure ("RVP") of the resulting alkylation product may be controlled by varying the ratios of the isoparaffin components in the alkylation feed. These and other discoveries will become readily apparent to those of skill in the art upon reading this specification.

Alkylation processes in general are well known to those of skill in the art. For example, see "Catalytic Alkylation", Petro/Chem Engineer, December 1961 and January 1962, "Alkylation will be key process in reformulated gasoline era", Oil & Gas Journal, Nov. 12, 1990, pp. 79–92, "$H_2SO_4$, HF processes compared, and new technologies revealed", Oil & Gas Journal, Nov. 26, 1990, pp. 70–77, and "Which alkylation—HF or $H_2SO_4$?", Hydrocarbon Processing, September 1985, all herein incorporated by reference. Additionally, alkylation is generally disclosed in U.S. Pat. Nos. 4,018,846; 4,225,740; 4,276,731; 4,371,731; 4,383,977; 4,404,418; 4,467,131; 4,513,165; 4,777,323, and 5,157,196; all herein also incorporated by reference.

In the practice of the alkylation process of the present invention, a mixture of paraffins is reacted with olefins in the presence of an alkylation catalyst to form high-octane gasoline components. The precise process steps and process conditions will vary somewhat depending upon the catalyst system utilized. It is anticipated that any suitable catalyst may be utilized, including liquid, solid or any other type of catalyst.

In the practice of the present invention, the reacting hydrocarbons will include $C_3$ to $C_5$ olefins as well as a suitable mixture of $C_4$ and $C_5$ isoparaffins. According to the present invention, the composition of the $C_4$ and $C_5$ isoparaffin mixture can be utilized to control the amount of and type of isoparaffins produced in the alkylation. Generally, as the amount of isopentane in the reactor feed is increased, the amount of isopentane produced decreases. Both isobutane and isopentane are consumed when the isopentane content of the reactor feed is between about 25 to 75 weight percent isopentane. When the isopentane content of the reactor feed is greater than about 75 weight percent isopentane, isobutane is produced.

In the alkylation of $C_5$ olefins with isobutane and with no isopentane in the reactor feed, the alkylate product will comprise in the range of about 11 to about 20 weight percent isopentane that is produced in the alkylation process. In the process of the present invention, the production of isopentane in the alkylation of $C_5$ olefins can be eliminated by utilizing an isobutane and isopentane feed stream that comprises in the range of about 10 to about 35 weight percent isopentane. Preferably, in the alkylation of $C_5$ olefins, the isobutane and isopentane feed stream that comprises in the range of about 15 to about 30 weight percent isopentane, and most preferably in the range of about 20 to about 25 weight percent isopentane. Of course, the amount of isopentane in the alkylation product may also be controlled by utilizing various percentages of isobutane and isopentane.

In the alkylation of $C_3$ and/or $C_4$ olefins with isobutane, the alkylate product will comprise in the range of about 3 to about 6.0 weight percent isopentane that is produced in the alkylation. In the process of the present invention, the production of isopentane in the alkylation of $C_3$ and/or $C_4$ olefins can be eliminated by utilizing an isobutane and isopentane feed stream that comprises in the range of about 1 to about 20 weight percent isopentane. Preferably, in the alkylation of $C_3$ and $C_4$ olefins, the isobutane and isopentane feed stream that comprises in the range of about 1 to about 15 weight percent isopentane, most preferably in the range of about 1 to about 10 weight percent isopentane. Again, the amount of isopentane in the alkylation product may be controlled by varying the percentages of isobutane and isopentane in the reactor feed.

In the alkylation of $C_3$ to $C_5$ olefins, the motor octane number ("MON") for the alkylation product may be increased above the research octane ("RON") by utilizing an isobutane and isopentane feed comprising greater than about 40 weight percent isopentane.

In the alkylation of $C_4$ and $C_5$ olefins, the alkylation yield may be increased by utilizing an isobutane and isopentane feed comprising greater than about 40 weight percent isopentane.

The alkylation process of the present invention is generally operated with ratios of isoparaffin to olefin in the feed streams to the reactor of greater than 1 to minimize undesired polymerization reactions. The isoparaffin to olefin ratio is generally in the range of about 2:1 to about 50:1, and preferably in the range of about 4:1 to about 20:1. Most preferably for hydrogen fluoride catalyzed alkylation, the isoparaffin to olefin ratio is in the range of about 10:1 to about 15:1. Most preferably for sulfuric acid catalyzed alkylation, the isoparaffin to olefin ratio is in the range of about 5:1 to about 10:1.

For the present invention the alkylation is generally carried out by contacting the catalyst and the reacting hydrocarbons in a reactor under closely controlled conditions. Alkylation reactions are very exothermic and require cooling to remove the heat of reaction from the reactor.

Reactor systems useful in the practice of the present invention include time-tank or pipe reactors, the Stratco® Contactor reactor, cascade reactors, gravity reactors, solid catalyst reactors, and the like, and other types of alkylation reactors known to those of skill in the alkylation art.

The catalyst and the reacting hydrocarbons are generally contacted together in the reactor utilizing a sufficient level of agitation to provide intimate contact between the two liquid phases. High levels of agitation are generally more important for sulfuric acid alkylation than for HF alkylation. The agitation is generally provided utilizing baffling, positioning of the impeller and by recycle streams.

Additionally, with some reactor systems, the hydrocarbons may be contacted with a liquid catalyst in the form of a fine dispersion in the liquid catalyst. The hydrocarbon droplet size utilized will be in the range of about 10 to about 1000 microns, preferably about 10 to about 100 microns to give good contact with the catalyst. The fine dispersion of hydrocarbons may be obtained by any suitable method, including introducing the hydrocarbons into the reactor at high velocity through nozzles, by utilizing a high shear mechanical device such as a centrifugal pump, by utilizing a static mixer, or by any other suitable method.

The alkylation catalyst utilized in the present alkylation invention may be any catalyst that will catalytically effect the reaction of the paraffins and olefins. Suitable catalysts include strong acid catalysts such as hydrofluoric acid, sulfuric acid, phosphoric acid, mixtures of sulfuric and phosphoric acids, metal halides such as aluminum chloride or aluminum bromide, certain complexes of aluminum chloride and sulfuric acid, and the like. It is also within the scope of this invention to effect the alkylation by contacting the alkylation reactants with a suitable solid alkylation catalyst. Solid catalysts such as macroreticular acidic ion exchange resins in the presence of $BF_3$ and zeolite catalysts can also be utilized. Also, solid catalysts such as acid washed silica treated with antimony pentafluoride, and preferably activated at low temperature with an alkane or isoalkane may be utilized. Preferably, the alkylation catalyst utilized in the present invention is hydrofluoric acid or sulfuric acid.

Acid strength of the catalyst utilized in the present invention is generally maintained high enough to avoid dilution of the acid catalyst but low enough to avoid excessive side reactions. For example, the range of useful strengths of sulfuric acid is generally in the range of about 86 to about 99 weight percent.

The volume ratio of catalyst to total hydrocarbons is generally in the range of about 10:1 to about 1:10, and preferably in the range of about 10:1 to about 1:2.

The alkylation temperature and pressure utilized in the present invention is generally selected to yield the desired alkylation products without undue detrimental effects upon the catalyst or alkylation reactants.

Generally, the alkylation temperature utilized in the present invention is in the range of about −60° F. to about 1000° F. Preferably, the alkylation temperature utilized in the present invention is in the range of about −40° F. to about 200° F., more preferably in the range of about 35° F. to about 200° F., and most preferably in the range of about 35° F. to about 125° F. It is observed that at lower temperatures the rate of reaction is generally slower, and at higher temperatures, some cracking, polymerization and carbon formation occurs. The alkylation temperature utilized will generally also be influenced by economy of equipment and operating costs.

Additionally, it is also noted that the most preferred alkylation temperatures will also vary depending upon the type of catalyst utilized. The upper limit on the alkylation temperature is generally selected to avoid undue temperature degradation of the catalyst and to keep the catalyst in the desired state. For example, with sulfuric acid catalysts, the alkylation temperature is most preferably in the range of about 40° F. to about 50° F. and generally requires some type of refrigeration, while the most preferable alkylation temperature when utilizing hydrogen fluoride catalysts is in the range of about 85° F. to about 115° F., which can generally be maintained utilizing cooling water. For solid catalysts such as acid washed silica treated with antimony pentafluoride, the prefered alkylation temperature is in the range of about −58° F. to about 212° F.

The alkylation pressure utilized in the present invention is generally selected to maintain at least a portion of, and preferably a majority of, the hydrocarbon reactants in a liquid phase. Generally, the reaction pressure is in the range of about atmospheric to about 5000 psi or more, preferably in the range of about 45 psi to about 1000 psi, and most preferably in the range of about 45 psi to about 250 psi.

Although the residence time of the reactants in the reactor or reaction zone can vary widely depending upon the process variables, the residence time is generally in the range of about 0.01 minutes to about 100 minutes. Preferably, the residence time is in the range of about 0.1 minutes to about 30 minutes, and more preferably in the range of about 1 minutes to about 20 minutes, and most preferably in the range of about 5 minutes to about 20 minutes.

EXAMPLES

Experiments were conducted to evaluate the present invention.

Figure 13:
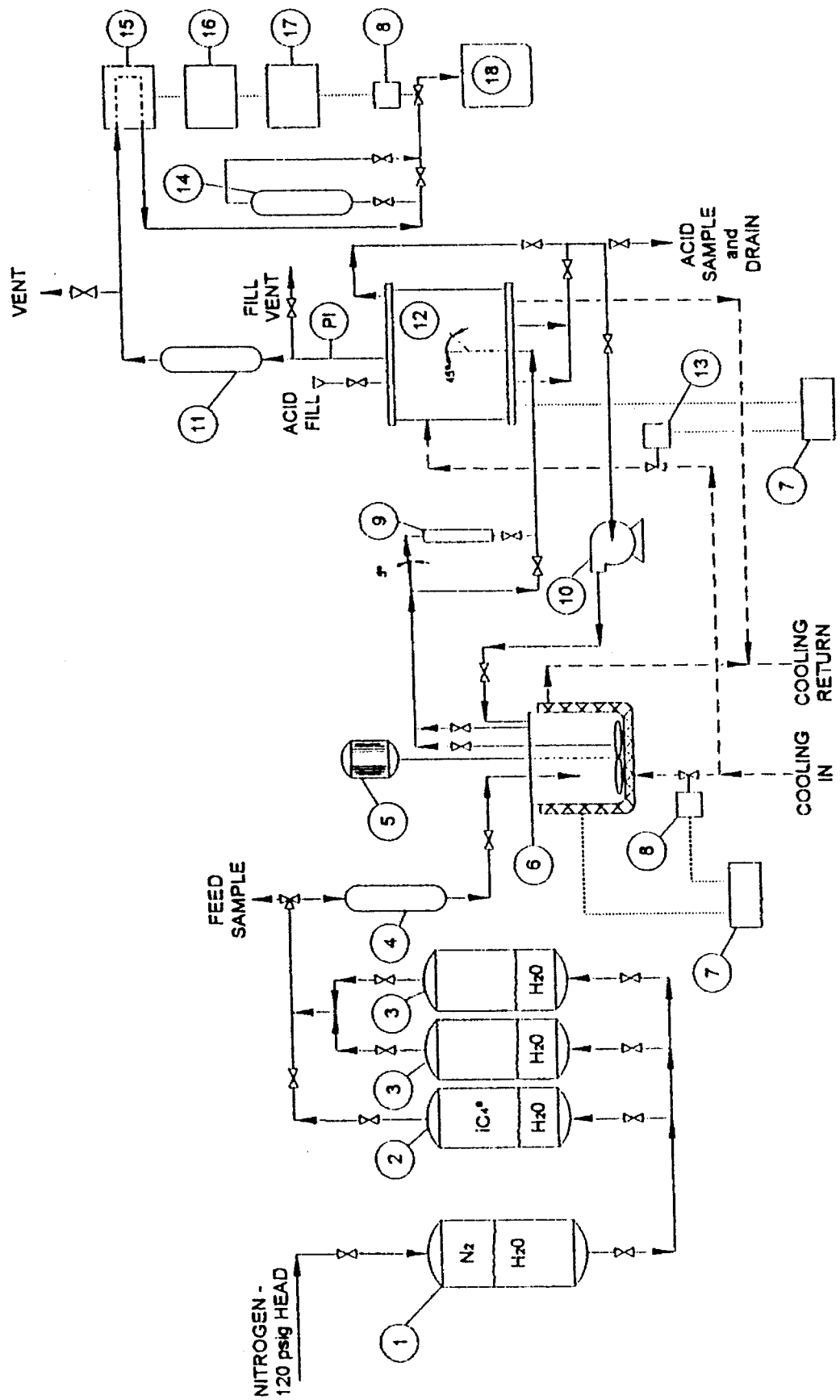
FIG. 13 is a schematic of the bench scale equipment utilized in the Examples, showing water cylinder 1, water flowmeter 2, fill isobutane 3, isoparaffin and olefin feed cylinder 4, molecular sieve 5, variable speed motor 6, 450 ml reactor 7, temperature readout controller 8, I-P valve actuator 9, temperature controller 10, multipoint temperature recorder 11, emulsion sight glass 12, variable speed acid recycle pump 13, caustic bed 14, glass settler 15, effluent sample cyclinder 16, micromotion flowmeter 17, micromotion transmitter with totalizer 18, flow controller 19, I-P valve actuator 20, and product vessel 21.

Bench scale equipment, as schematically represented in FIG. 13, was used for this study. FIG. 13 is a schematic of the bench scale equipment utilized in these Examples, showing water cylinder 1, water flowmeter 2, fill isobutane 3, isoparaffin and olefin feed cylinder 4, molecular sieve 5, variable speed motor 6, 450 ML reactor 7, temperature readout controller 8, I-P valve actuator 9, temperature controller 10, multi-point temperature recorder 11, emulsion sight glass 12, variable speed acid recycle pump 13, caustic bed 14, glass settler 15, effluent sample cyclinder 16, flowmeter 17, transmitter with totalizer 18, flow controller 19, I-P valve actuator 20, and product vessel 21.

The mixer speed for reactor 7 is maintained at about 1100 rpm. Five gallon water cylinder 1 was pressured to approximately 120 psi with nitrogen. The water flows from the water cylinder 1 through flowmeter 2 and into the bottom of cylinder 4 mixed isobutane/olefin feed. The hydrogen feed was fed through molecular sieve 5 to remove water from the feed, and then into the reactor 7. Effluent was drawn off the bottom of the reactor 7 and then directed into the settler 15. Acid is drawn from the bottom of the settler 15 and recirculated back to the reactor 7. The hydrocarbon product flows from the top of the settler 15 through caustic bed 14, and into the product cylinder 21.

A large batch of synthetic acid was prepared as follows. A "stock" supply of low-strength acid is generated. Commercial-grade 2-butenes are sparged into a volume of fresh, water-white acid (98.5–99 wt % $H_2SO_4$). The acid is kept at a temperature no more than 100° F. to minimize extended polymerization of the forming acid-soluble oils. Samples of the acid are analysed periodically to determine the diluted acid strength. When the acid reaches approximately 90 wt % $H_2SO_4$, the hydrocarbon flow is stopped and the acid is refrigerated until needed. Knowing the weight percent of the fresh and synthetic acids, it is possible to mix calculated amounts of the fresh and "stock" synthetic acids together to form a volume of specific strength acid. Using a similar technique, non-synthetic spent acid-removed from the pilot plant at the end of an experiment-can be "boosted" to a target strength with the calculated volume of fresh acid (98.5–99 wt % $H_2SO_4$). This technique is used when a series of experiments utilizing the same (or effectively similar) feed is run over the course of a few days. This technique cuts down on waste acid and has no noticeable side effects as long as the feed composition remains constant or consistent.

Alternatively, some synthetic used sulfuric acid was prepared by first spiking fresh acid with oleum to raise the acidity to 98.5–99% $H_2SO_4$. Butene-1 was then bubbled through the acid until the acidity is reduced to approximately 97.5% $H_2SO_4$. Then 2-butenes are bubbled through the acid until an acidity of 94.5%–95% $H_2SO_4$ is obtained.

The system described was then charged with 500 ML of synthetic used acid prepared as directed. An average acid to hydrocarbon volume ratio in the reactor of 45% to 65% was maintained throughout the runs. Usually the acid to hydrocarbon ratio was maintained at 50%–55% (v/v). The settler temperature was monitored at the bottom of the settler and where the acid effluent exits. The temperature of effluent was kept at about the reactor temperature while the temperature of the acid exiting the settler is maintained at about the reactor temperature.

A sample of acid and product was analyzed about every 1.5 hours. The acid was sampled by first purging 5 ML of acid through a sampling valve followed by collecting an additional 5 ML in a centrifuge tube. The acid sample was then centrifuged for 15 minutes and about 0.5 g (weighed to +/−0.1 mg) was titrated to 5.8 pH end point with standarized aqueous NaOH. The alkylate samples were analyzed by a standard gas chromatograph (G.C.) procedure. The G.C. was equipped with a 50 m capillary column which could separate hydrocarbons up to $C_{14}$.

Using the previously described reaction scheme, the following Examples 1–4 were conducted.

Example No. 1

Alkylation of propylene with approximately 23 wt % of the isoparaffins in the feed ($iC_4+iC_5$) being isopentane.
Operating Conditions:
50° F. Reaction Temperature
0.30 hr$^{-1}$ olefin space velocity
96 wt % $H_2SO_4$ starting acidity
50 vol % acid/HC ratio in reactor
6.9 $iC_4$ olefin molar ratio
8.7 Total isoparaffin/olefin molar ratio

| Feed Composition wt %/component | Settler Effluent Composition wt %/component |
|---|---|
| 0.6 propane | 1.1 propane |
| 7.6 propylene | 60.8 isobutane |
| 74.5 isobutane | 1.5 n-butane |
| 1.6 n-butane | 18.2 isopentane |
| 0.0 mixed butylenes | 0.7 n-pentane |
| 22.4 isopentane | 0.7 $C_6$ isoparaffins |
| 0.7 n-pentane | 10.8 $C_7$ isoparaffins |
| 0.1 mixed pentenes | 3.6 $C_8$ isoparaffins |
|  | 0.7 $C_9$ isoparaffins |
|  | 1.5 $C_{10}$ isoparaffins |
|  | 0.4 $C_{11+}$ isoparaffins |
| Results |  |
| Acid Consumption | 1.88 lb/gal $C_{6+}$ |
| Yield | 1.70 vol $C_{6+}$ net alkylate/vol olefin |
| $iC_4$ consumption | 1.51 vol $iC_4$/vol olefin |
| $iC_5$ consumption | 0.62 vol $iC_5$/vol olefin |
| ASTM D-86 $T_{90}$ | 283° F. |
| ASTM D-86 end pt | 403° F. |
| Estimated RON | 87.6 |
| Estimated MON | 86.8 |

Example No. 2

Alkylation of butylenes with approximately 11 wt % of the isoparaffins in the feed ($iC_4+iC_5$) being isopentane.
Operating Conditions:
50° F. Reaction Temperature
0.30 hr$^{-1}$ olefin space velocity
94.85 wt % $H_2SO_4$ starting acidity
53 vol % acid/HC ratio in reactor
7.8 $iC_4$ olefin molar ratio
8.9 Total isoparaffin/olefin molar ratio

| Feed Composition wt %/component | Settler Effluent Composition wt %/component |
|---|---|
| 0.6 propane | 0.5 propane |
| 0.0 propylene | 67.6 isobutane |
| 77.8 isobutane | 1.7 n-butane |
| 1.8 n-butane | 8.9 isopentane |
| 9.6 mixed butylenes | 0.3 n-pentane |
| 10.0 isopentane | 0.9 $C_6$ isoparaffins |
| 0.3 n-pentane | 0.8 $C_7$ isoparaffins |
| 0.0 mixed pentenes | 15.2 $C_8$ isoparaffins |
|  | 2.2 $C_9$ isoparaffins |
|  | 0.7 $C_{10}$ isoparaffins |
|  | 1.2 $C_{11+}$ isoparaffins |
| Results |  |
| Acid Consumption | 0.29 lb/gal $C_{6+}$ |
| Yield | 1.87 vol $C_{6+}$ net alkylate/vol olefin |
| $iC_4$ consumption | 1.15 vol $iC_4$/vol olefin |
| $iC_5$ consumption | 0.11 vol $iC_5$/vol olefin |
| ASTM D-86 $T_{90}$ | 282° F. |
| ASTM D-86 end pt | 431° F. |
| Estimated RON | 94.7 |
| Estimated MON | 92.7 |

Example No. 3

Alkylation of amylenes with approximately 23 wt % of the isoparaffins in the feed ($iC_4+iC_5$) being isopentane. Very little isopentane was consumed.
Operating Conditions:
50° F. Reaction Temperature
0.30 hr$^{-1}$ olefin space velocity
95 wt % $H_2SO_4$ starting acidity
50 vol % acid/HC ratio in reactor
6.7 $iC_4$ olefin molar ratio
8.3 Total isoparaffin/olefin molar ratio

| Feed Composition wt %/component | Settler Effluent Composition wt %/component |
|---|---|
| 0.4 propane | 0.4 propane |
| 0.0 propylene | 55.9 isobutane |
| 65.5 isobutane | 1.4 n-butane |
| 1.5 n-butane | 19.7 isopentane |
| 0.1 mixed butylenes | 0.6 n-pentane |
| 20.0 isopentane | 1.3 $C_6$ isoparaffins |
| 0.7 n-pentane | 0.5 $C_7$ isoparaffins |
| 1.4 2-methyl-1-butene | 6.6 $C_8$ isoparaffins |
| 1.4 1-pentene | 8.8 $C_9$ isoparaffins |
| 0.3 2-methyl-1-butene | 3.7 $C_{10}$ isoparaffins |
| 4.0 2-pentenes (t & c) | 1.0 $C_{11+}$ isoparaffins |
| 4.3 2-methyl-2-butene |  |
| 0.5 cyclopentene |  |
| Results |  |
| Acid Consumption | 1.24 lb/gal $C_{6+}$ |
| Yield | 1.71 vol $C_{6+}$ net alkylate/vol olefin |
| $iC_4$ consumption | 0.95 vol $iC_4$/vol olefin |
| $iC_5$ consumption | 0.03 vol $iC_5$/vol olefin |
| ASTM D-86 $T_{90}$ | 333° F. |
| ASTM D-86 end pt | 486° F. |
| Estimated RON | 86.2 |
| Estimated MON | 87.6 |

Example No. 4

Alkylation of pentenes with approximately 99 wt % of the isoparaffins in the feed ($iC_4+iC_5$) being isopentane. This example shows isobutane being produced and the increased yield of alkylate when isopentane is the major feed isoparaffin.
Operating Conditions:
50° F. Reaction Temperature
0.30 hr$^{-1}$ olefin space velocity
95 wt % $H_2SO_4$ starting acidity
49 vol % acid/HC ratio in reactor
0.1 $iC_4$ olefin ratio 9.2 Total isoparaffin/olefin molar ratio

| Feed Composition wt %/component | Settler Effluent Composition wt %/component |
|---|---|
| 0.0 propane | 0.0 propane |
| 0.0 propylene | 4.9 isobutane |
| 0.5 isobutane | 0.1 n-butane |
| 0.1 n-butane | 69.2 isopentane |
| 7.6 mixed butylenes | 2.3 n-pentane |
| 89.6 isopentane | 4.3 $C_6$ isoparaffins |
| 2.3 n-pentane | 0.9 $C_7$ isoparaffins |
| 0.0 pentenes | 2.7 $C_8$ isoparaffins |
|  | 7.8 $C_9$ isoparaffins |
|  | 6.3 $C_{10}$ isoparaffins |
|  | 1.4 $C_{11+}$ isoparaffins |
| Results |  |
| Acid Generation | 0.65 lb/gal $C_{6+}$ |
| Yield | 2.63 vol $C_{6+}$ net alkylate/vol olefin |
| $iC_4$ consumption | 0.64 vol $iC_4$/vol olefin |
| $iC_5$ consumption | 2.60 vol $iC_5$/vol olefin |
| ASTM D-86 $T_{90}$ | 325° F. |
| ASTM D-86 end pt | 439° F. |
| Estimated RON | 80.7 |
| Estimated MON | 84.2 |

Example results are presented in the following FIGS. 1–12.

FIG. 1 shows the relationship between sulfuric acid catalyst consumption and the weight percent of isopentane in the isobutane and isopentane feed for various olefins. This relationship is of importance, as consumption or dilution of the sulfuric acid with acid soluble oils is one of the major operation costs for an alkylation unit. For example, in the alkylation of isobutane with butylenes, acid costs typically represent approximately 30% of the total operating expense. While all of the olefins tested exhibited an increased acid consumption with increased isopentane percentages, the change in acid consumption when increasing amounts of isopentane were alkylated with butylenes was much less than for either propylene or amylenes. Thus, in terms of limiting acid consumption increases, it appears preferable to alkylate isopentane with butylenes.

Figure 2:
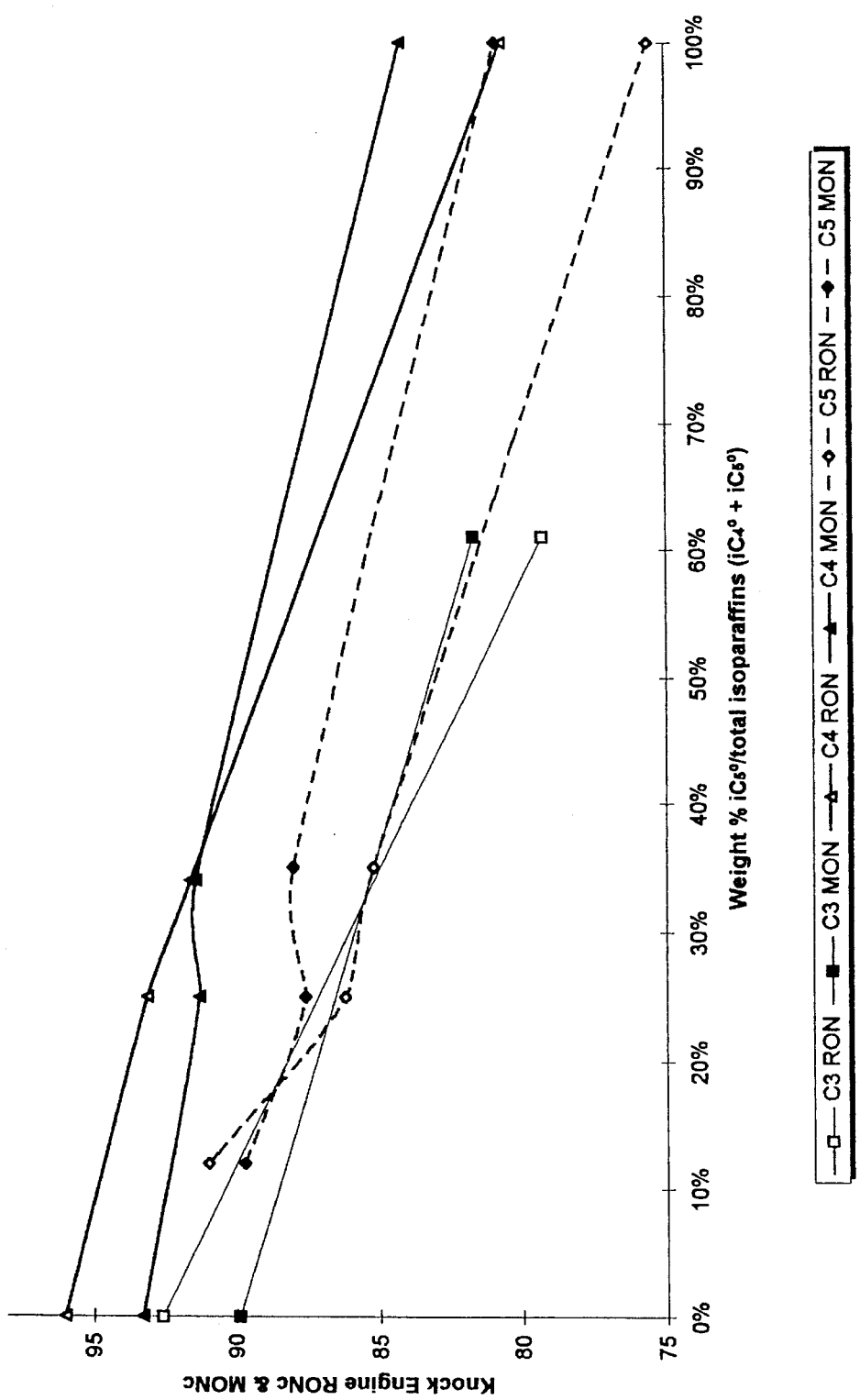
FIG. 2 is a graph that shows the trend in octane numbers as isopentane is substituted for isobutane in the reactor feed.

FIG. 2 shows the trend in octane numbers as isopentane is substituted for isobutane in the reactor feed. These octane numbers were determined by actual knock engine tests of depentanized alkylate. As the amount of isopentane is increased, lower quality alkylate is produced. However, as shown in FIG. 2, as the isopentane percentage in the feed is increased beyond about 30 to about 40 weight percent, the motor octane numbers ("MON") are greater than the research octane numbers ("RON").

Figure 3:
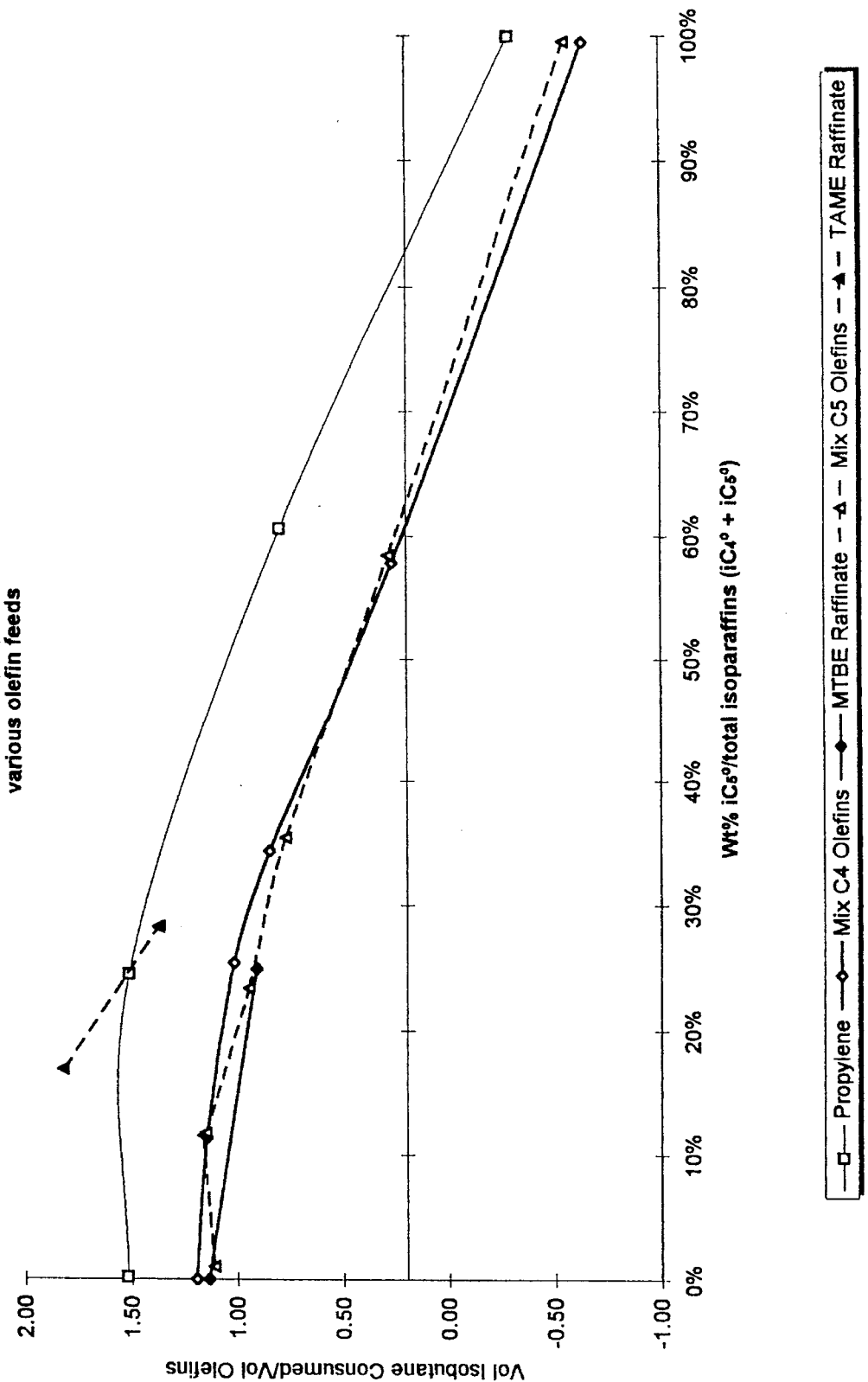
FIG. 3 is a graph of isobutane consumption versus the weight percentage of isopentane in the reactor feed for various olefins.

FIG. 3 is a graph of isobutane consumption versus the weight percentage of isopentane in the reactor feed for various olefins. FIG. 3 shows that there is a decrease in isobutane consumption as the percentage of isopentane in the reactor feed increases. As shown, the decrease in isobutane consumption is somewhat flat until isopentane comprises about 30 weight percent of the reactor feed, at which point isobutane consumption increases rapidly. When the level of isopentane in the reactor feed exceeds about 70 weight percent for the mixtures of $C_4$ and $C_5$ olefins, the reaction equilibrium favors the net production of isobutane.

Figure 4:
FIG. 4 is a graph of isopentane consumption versus the weight percentage of isopentane in the reactor feed for various olefins.

FIG. 4 is a graph of isopentane consumption versus the weight percentage of isopentane in the reactor feed for various olefins. For all of the olefin feeds, with no isopentane in the feed, some isopentane is produced in the alkylation.

Figure 5:
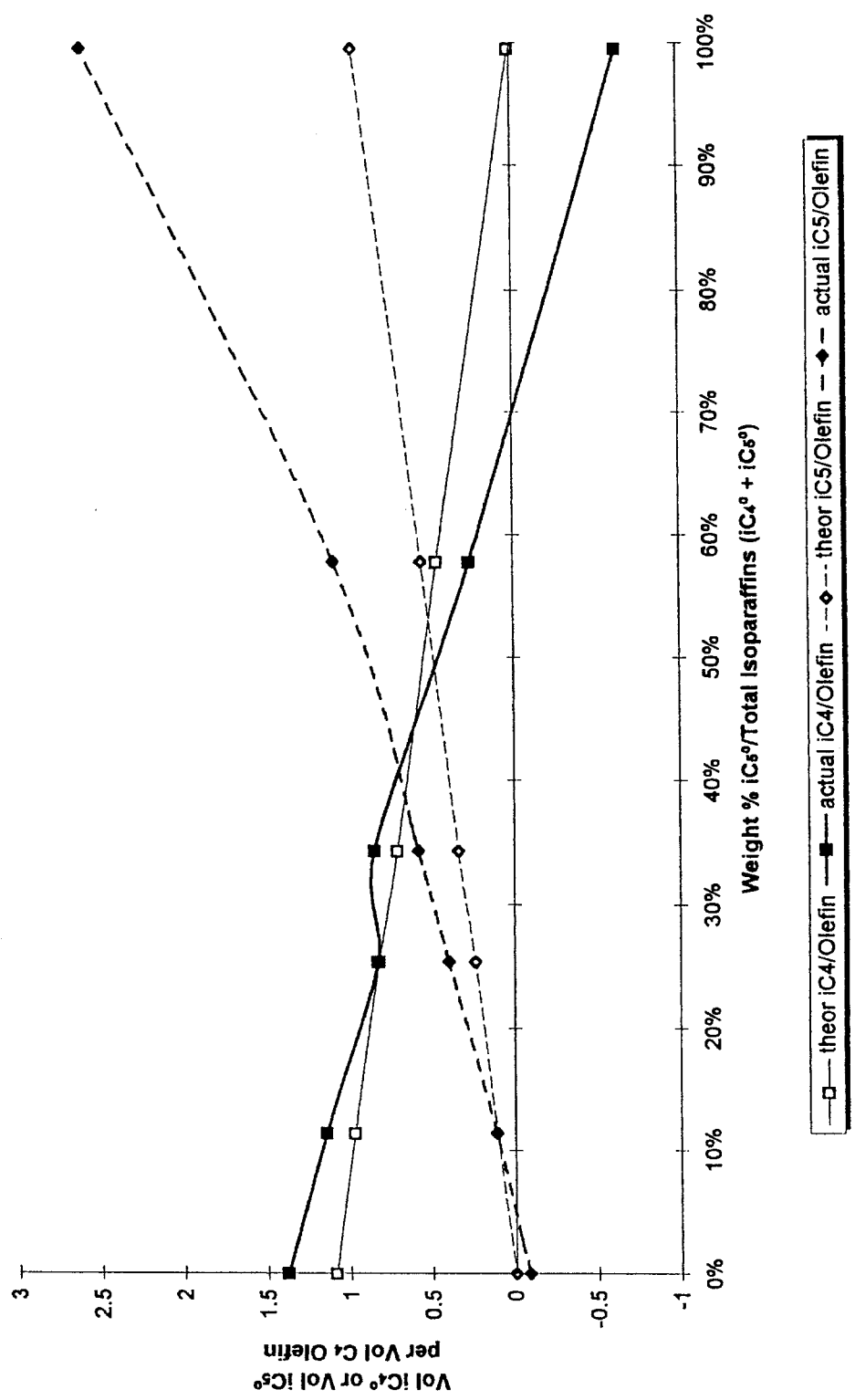
FIG. 5 is a graph of isobutane and isopentane consumption with mixed butenes, showing both actual data and calculated data.
Figure 6:
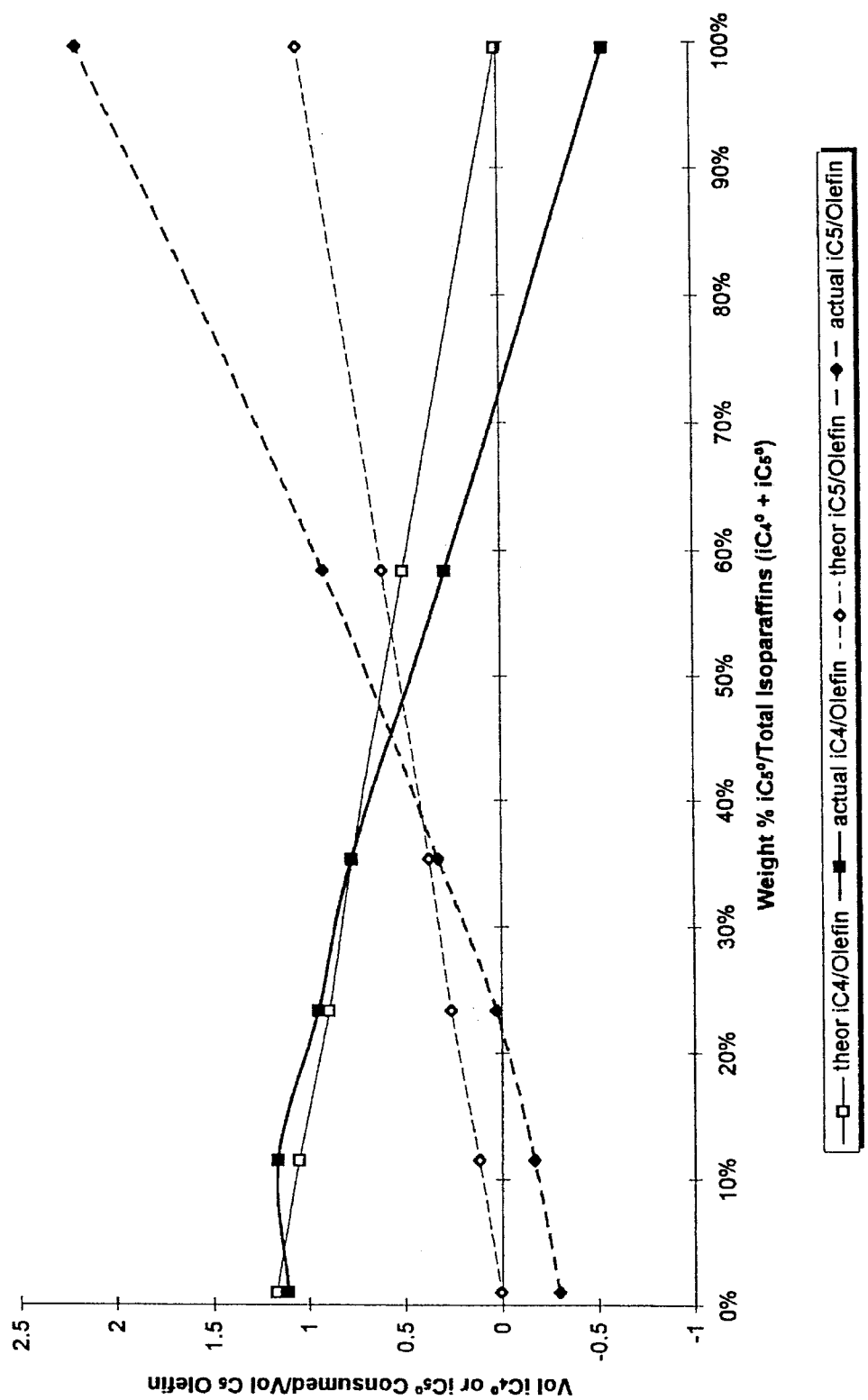
FIG. 6 is a graph of isobutane and isopentane consumption with mixed pentenes, showing both actual data and calculated data.

FIG. 5 is a graph of isobutane and isopentane consumption with mixed butenes, showing both actual data and calculated data. FIG. 6 is a graph of isobutane and isopentane consumption with mixed pentenes, showing both actual data and calculated data. The calculated isoparaffin consumption numbers are based on a stoichiometric reaction of isobutane or isopentane with butylenes (FIG. 5) or amylenes (FIG. 6).

Figure 7:
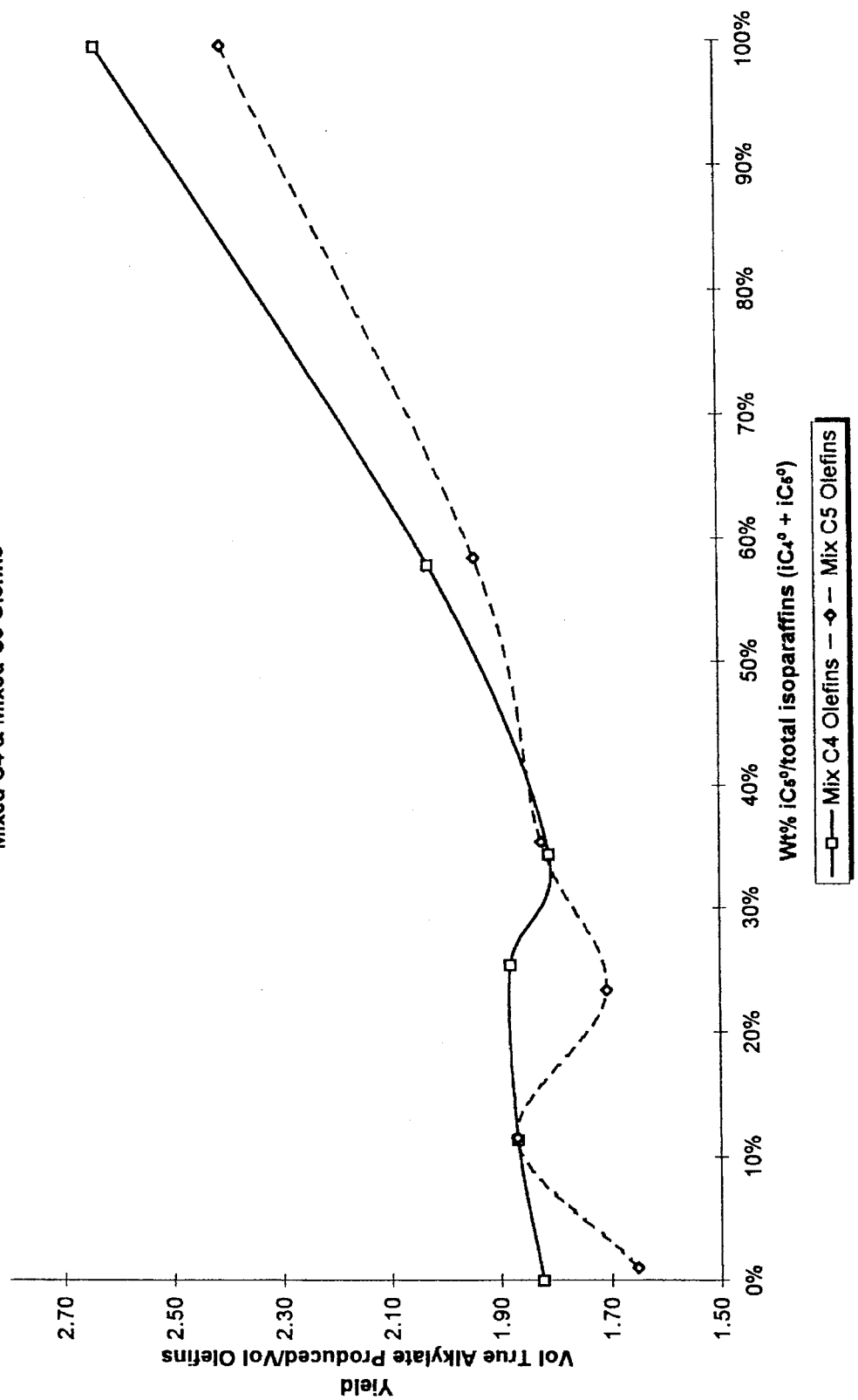
FIG. 7 is a graph of the yield of true alkylate produced versus the weight percent of isopentane in the reactor feed for $C_4$ and $C_5$ olefin feeds.
Figure 8:
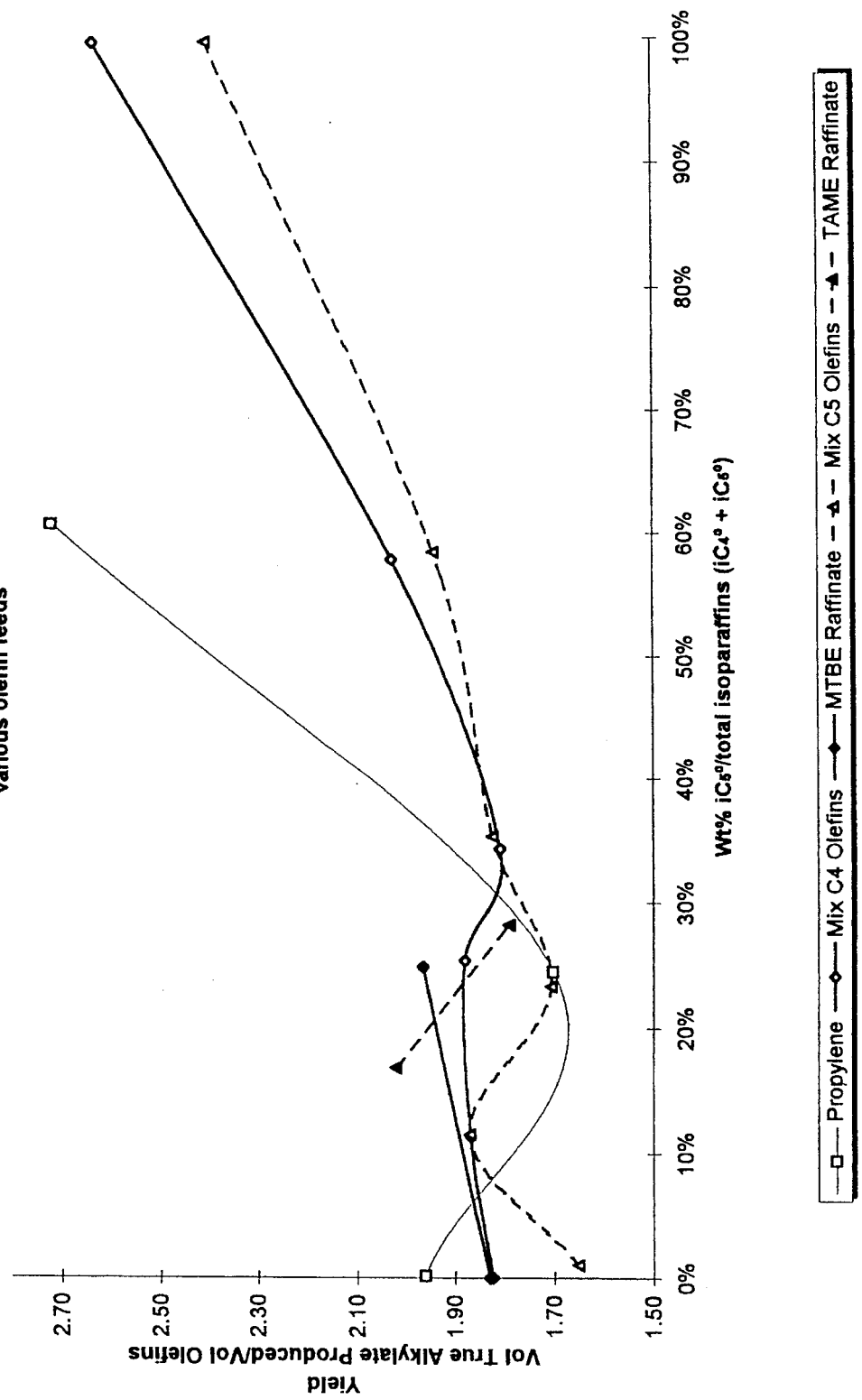
FIG. 8 is a graph of the yield of true alkylate produced versus the weight percent of isopentane in the reactor feed for various olefin feeds.

FIGS. 7 and 8 are graphs of the yield of true alkylate produced versus the weight percent of isopentane in the reactor feed for $C_4$ and $C_5$ olefin feeds (FIG. 7) and for various olefin feeds (FIG. 8). The graphs show a gradual increase in the volume yield of true alkylate produced as isopentane replaces isobutane. $C_5$ olefins show a gradual increase throughout the entire range. $C_4$ olefins show minimal yield increase when the isopentane feed percentage is less than about 40 weight percent. Above 40 weight percent, the yield increase similar to that with $C_5$ olefins.

Figure 9:
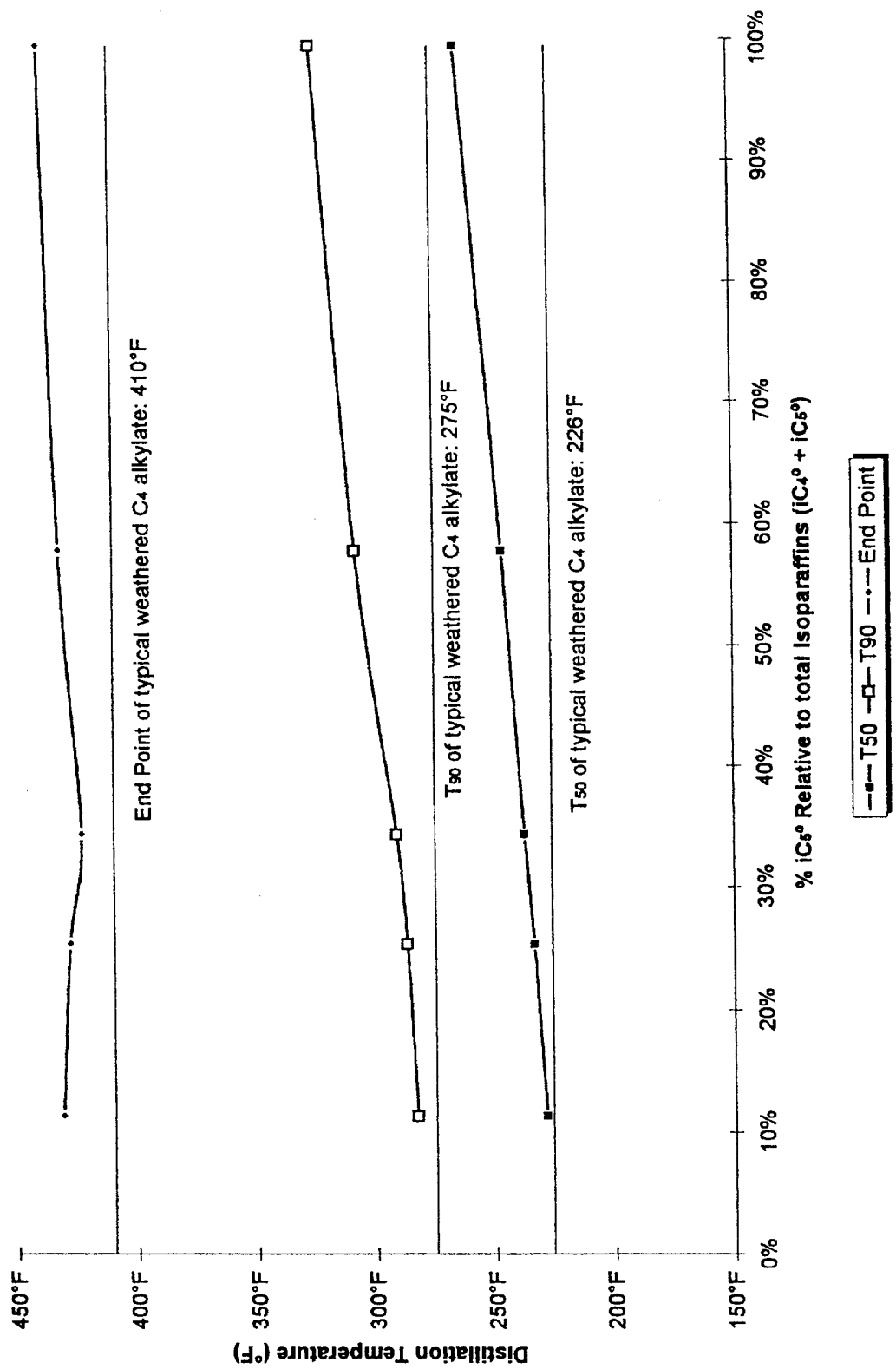
FIG. 9 is a graph of distillation temperature versus the weight percentage of isopentane in the reactor feed for the alkylation of $C_4$ olefins.
Figure 10:
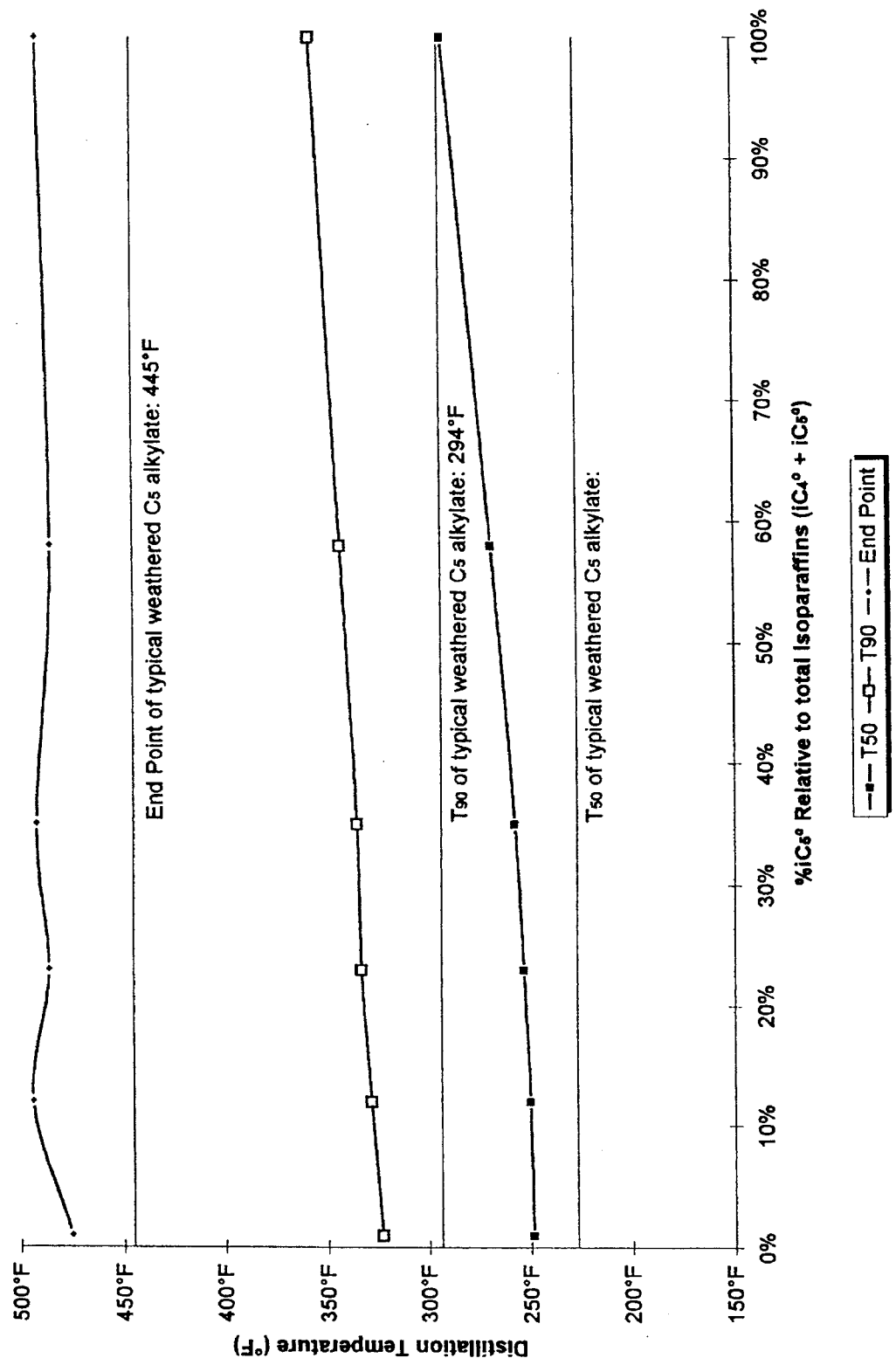
FIG. 10 is a graph of distillation temperature versus the weight percentage of isopentane in the reactor feed for the alkylation of $C_5$ olefins.

FIGS. 9 and 10 are graphs of distillation temperature versus the weight percentage of isopentane in the reactor feed for the alkylation of $C_4$ olefins (FIG. 9) and for the alkylation of $C_5$ olefins (FIG. 10).

Figure 11:
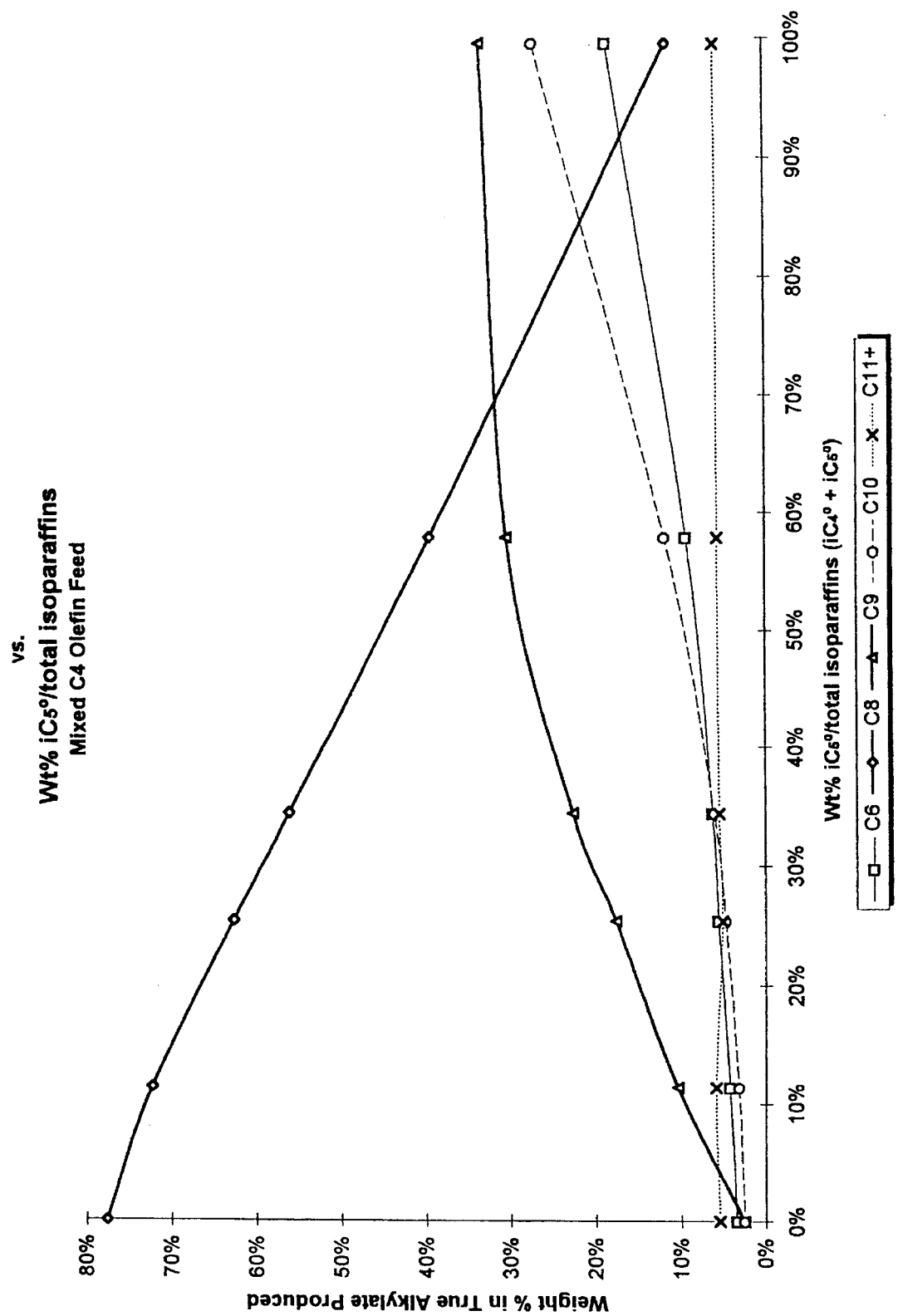
FIG. 11 is a graph of the weight percent of carbon number groups in the alkylate product versus the weight percent of isopentane in the reactor feed for a mixed $C_4$ olefin feed.
Figure 12:
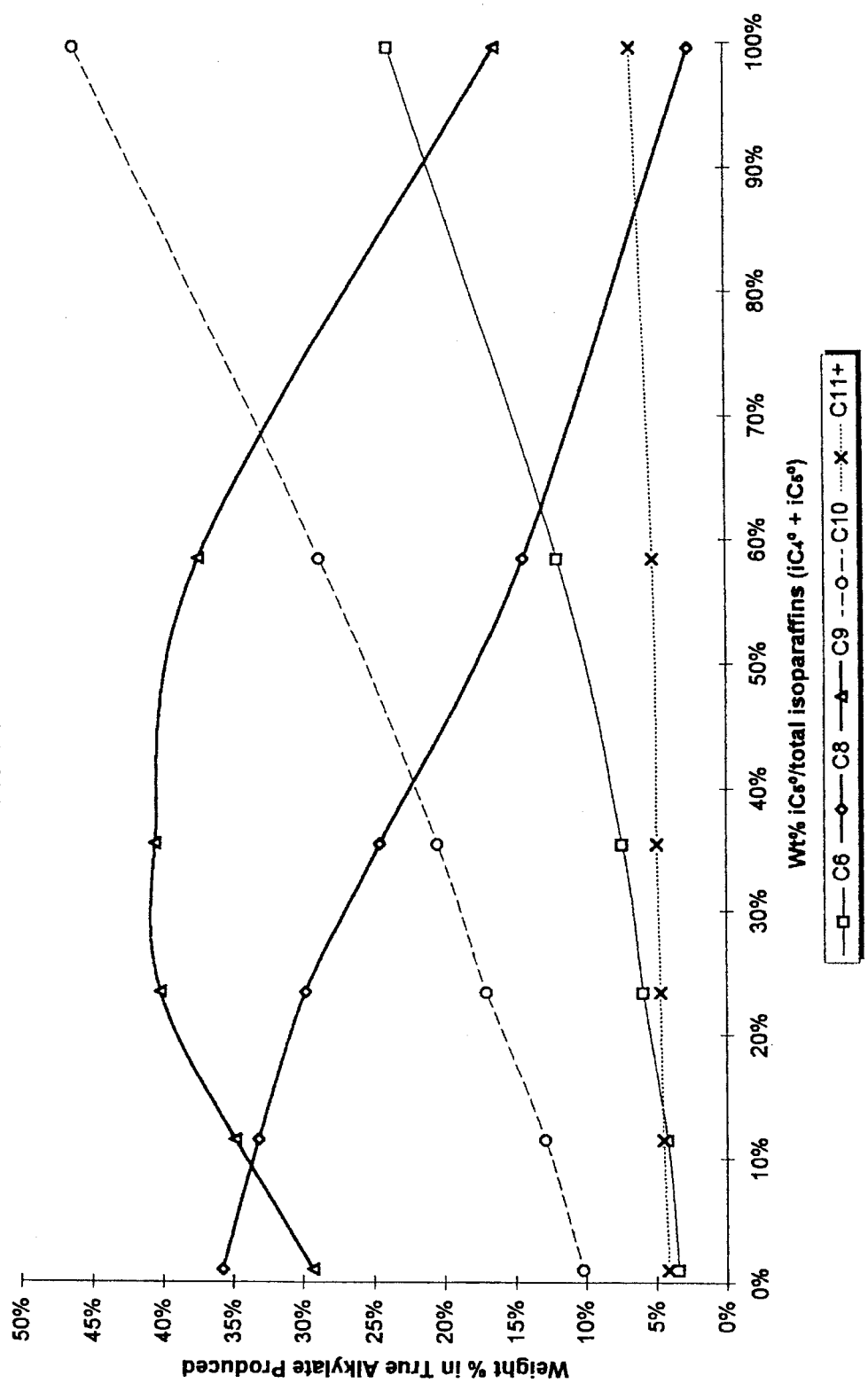
FIG. 12 is a graph of the weight percent of carbon number groups in the alkylate product versus the weight percent of isopentane in the reactor feed for a mixed $C_5$ olefin feed.

FIG. 11 is a graph of the weight percent of carbon number groups in the alkylate product versus the weight percent of isopentane in the reactor feed for a mixed $C_4$ olefin feed. FIG. 12 is a graph of the weight percent of carbon number groups in the alkylate product versus the weight percent of isopentane in the reactor feed for a mixed $C_5$ olefin feed.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled the art to which this invention pertains.

We claim:

1. A process for producing an alkylate product by alkylating $C_3$ to $C_4$ olefins with an isoparaffin mixture comprising isobutane and isopentane in which the amount of isopentane produced in the reaction is less than or equal to the amount of isopentane consumed in the reaction, the process comprises contacting in a reaction zone $C_3$ to $C_4$ olefins with an isoparaffin mixture comprising isobutane and isopentane in the presence of an alkylation catalyst, wherein the isoparaffin mixture comprises in the range of about 1 to about 20 weight percent isopentane based on the total weight of isobutane and isopentane.

2. The process of claim 1 wherein the alkylate product comprises in the range of about 3 to about 4.5 weight percent isopentane that is produced by the alkylating of claim 1.

3. The process of claim 1 wherein the ratio of isoparafin mixture to olefins is in the range of about 2:1 to about 50:1.

4. The process of claim 1 wherein the alkylation temperature is in the range of about –40° F. to about 200° F., the reaction pressure is in the range of about 45 psi to about 1000 psi, and residence time in the reaction zone is in the range of about 0.01 minutes to about 100 minutes.

5. The process of claim 1 wherein the alkylate product comprises in the range of about 3 to about 4.5 isopentane that is produced by the alkylating of claim 1, wherein the ratio of isoparafin mixture to olefins is in the range of about 2:1 to about 50:1, wherein the alkylation temperature is in the range of about −40° F. to about 200° F., the reaction pressure is in the range of about 45 psi to about 1000 psi, and residence time in the reaction zone is in the range of about 0.01 to about 100 minutes.

6. The process of claim 1 wherein the ratio of isoparafin mixture to olefins is in the range of about 4:1 to about 20:1.

7. The process of claim 1 wherein the ratio of isoparafin mixture to olefins is in the range of about 10:1 to about 15:1.

8. The process of claim 1 wherein the isoparaffin mixture comprises in the range of about 1 to about 15 weight percent isopentane based on the total weight of isobutane and isopentane.

9. The process of claim 8 wherein the ratio of isoparafin mixture to olefins is in the range of about 2:1 to about 50:1.

10. The process of claim 8 wherein the ratio of isoparafin mixture to olefins is in the range of about 4:1 to about 20:1.

11. The process of claim 8 wherein the ratio of isoparafin mixture to olefins is in the range of about 10:1 to about 15:1.

12. The process of claim 1 wherein the isoparaffin mixture comprises in the range of about 1 to about 10 weight percent isopentane based on the total weight of isobutane and isopentane.

13. The process of claim 12 wherein the ratio of isoparafin mixture to olefins is in the range of about 2:1 to about 50:1.

14. The process of claim 12 wherein the ratio of isoparafin mixture to olefins is in the range of about 4:1 to about 20:1.

15. The process of claim 12 wherein the ratio of isoparafin mixture to olefins is in the range of about 10:1 to about 15:1.

* * * * *